United States Patent
Ishii et al.

(10) Patent No.: US 9,044,135 B2
(45) Date of Patent: Jun. 2, 2015

(54) ENDOSCOPE APPARATUS AND ELECTRONIC APPARATUS

(75) Inventors: Norihiro Ishii, Akishima (JP); Takahiro Sugai, Kokubunji (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 218 days.

(21) Appl. No.: 13/457,211

(22) Filed: Apr. 26, 2012

(65) Prior Publication Data

US 2012/0323076 A1 Dec. 20, 2012

(30) Foreign Application Priority Data

Jun. 16, 2011 (JP) ................................. 2011-134659

(51) Int. Cl.
| | |
|---|---|
| *A61B 1/00* | (2006.01) |
| *H01L 23/053* | (2006.01) |
| *A61B 1/12* | (2006.01) |
| *H05K 1/11* | (2006.01) |
| *H05K 3/34* | (2006.01) |
| *H01L 23/498* | (2006.01) |

(52) U.S. Cl.
CPC ........... *A61B 1/00004* (2013.01); *A61B 1/0011* (2013.01); *A61B 1/121* (2013.01); *H05K 1/111* (2013.01); *H05K 3/3436* (2013.01); *H05K 2201/094* (2013.01); *H05K 2201/10719* (2013.01); *H05K 2201/10977* (2013.01); *H01L 23/49805* (2013.01); *H01L 2924/15153* (2013.01); *H01L 2924/15313* (2013.01); *H01L 2924/16195* (2013.01); *H01L 23/053* (2013.01); *H01L 2924/0002* (2013.01)

(58) Field of Classification Search
CPC .. A61B 1/0011; A61B 1/121; A61B 1/00004; H05K 1/111; H05K 3/3436; H05K 2201/094; H01L 23/053

USPC .............. 600/133, 109, 130; 348/76, 65, 294; 257/783, 787; 438/118; 174/259, 260
See application file for complete search history.

(56) References Cited

U.S. PATENT DOCUMENTS

| | | | | |
|---|---|---|---|---|
| 4,372,037 A | * | 2/1983 | Scapple et al. | ................... 29/613 |
| 4,577,056 A | * | 3/1986 | Butt | ............................ 174/50.5 |
| 4,732,952 A | * | 3/1988 | Hirsekorn et al. | ............. 525/530 |
| 4,783,514 A | * | 11/1988 | Kirchhoff et al. | ............. 526/281 |
| 4,795,791 A | * | 1/1989 | Koenig et al. | ................. 525/523 |

(Continued)

FOREIGN PATENT DOCUMENTS

| | | | |
|---|---|---|---|
| JP | H07-278268 A | | 10/1995 |
| JP | H08-083799 A | | 3/1996 |

(Continued)

*Primary Examiner* — John P Leubecker
(74) *Attorney, Agent, or Firm* — Knobbe, Martens, Olson & Bear LLP

(57) ABSTRACT

According to one exemplary embodiment, an endoscope apparatus includes: an insertion unit that is an object to be disinfected by boiling; an operation unit connected to the insertion part; a main unit connected to the operation unit; a first circuit board embedded in the main unit; a first electronic component electrically connected to the first circuit board via a first solder; a second circuit board embedded in at least any one of the insertion unit and the operation unit; a second electronic component electrically connected to the second circuit board via a second solder having higher stress resistance than that of the first solder; and a bonding member bonded to the second electronic component and the second circuit board, the bonding member having a glass transition point higher than that of the second circuit board.

3 Claims, 14 Drawing Sheets

(56) References Cited

U.S. PATENT DOCUMENTS

| | | | |
|---|---|---|---|
| 4,860,444 A * | 8/1989 | Herrell et al. | 29/840 |
| 4,937,785 A * | 6/1990 | Deering | 710/306 |
| 5,818,113 A * | 10/1998 | Iseki et al. | 257/778 |
| 6,018,188 A * | 1/2000 | Yusa | 257/668 |
| 6,080,101 A | 6/2000 | Tatsuno et al. | 600/112 |
| 6,328,691 B1 * | 12/2001 | Rudischhauser | 600/176 |
| 6,413,353 B2 * | 7/2002 | Pompeo et al. | 156/307.3 |
| 6,486,411 B2 * | 11/2002 | Miura et al. | 174/256 |
| 8,233,757 B2 * | 7/2012 | Kathman et al. | 385/14 |
| 8,602,972 B2 * | 12/2013 | Unsai | 600/110 |
| 2001/0016679 A1 * | 8/2001 | Futatsugi et al. | 600/133 |
| 2002/0171157 A1 * | 11/2002 | Soga et al. | 257/783 |
| 2005/0121806 A1 * | 6/2005 | Sangiorgi | 257/787 |
| 2009/0310321 A1 * | 12/2009 | Sugai et al. | 361/783 |
| 2010/0171414 A1 | 7/2010 | Tanikawa et al. | |
| 2011/0001233 A1 * | 1/2011 | Iwase et al. | 257/737 |

FOREIGN PATENT DOCUMENTS

| | | |
|---|---|---|
| JP | H10-284647 A | 10/1998 |
| JP | 2008-130738 A | 6/2008 |
| WO | WO 2008-153125 A1 | 12/2008 |

* cited by examiner

US 9,044,135 B2

ENDOSCOPE APPARATUS AND ELECTRONIC APPARATUS

CROSS REFERENCE TO RELATED APPLICATION(S)

The application is based upon and claims the benefit of priority from Japanese Patent Application No. 2011-134659 filed on Jun. 16, 2011; the entire contents of which are incorporated herein by reference.

FIELD

Embodiments described herein relate generally to an endoscope apparatus and electronic apparatus.

BACKGROUND

Electronic components such as a land grid array (LGA) are mounted on a printed circuit board by soldering. These electronic components may be in a high temperature state according to its usage environments. For example, a CMOS sensor mounted in the endoscope is in a high temperature state when the endoscope is sterilized by boiling the endoscope by an autoclave.

BRIEF DESCRIPTION OF THE DRAWINGS

Exemplary embodiments of the present invention will be described in detail based on the following figures, wherein.

DETAILED DESCRIPTION OF THE EXEMPLARY EMBODIMENTS

According to one embodiment, an endoscope apparatus includes: an insertion unit that is an object to be disinfected by boiling; an operation unit connected to the insertion part; a main unit connected to the operation unit; a first circuit board embedded in the main unit; a first electronic component configured to be electrically connected to the first circuit board via a first solder; a second circuit board embedded in at least any one of the insertion unit and the operation unit; a second electronic component configured to be electrically connected to the second circuit board via a second solder having higher stress resistance than that of the first solder; and a bonding member bonded to the second electronic component and the second circuit board, the bonding member having a glass transition point higher than that of the second circuit board.

Figure 1:
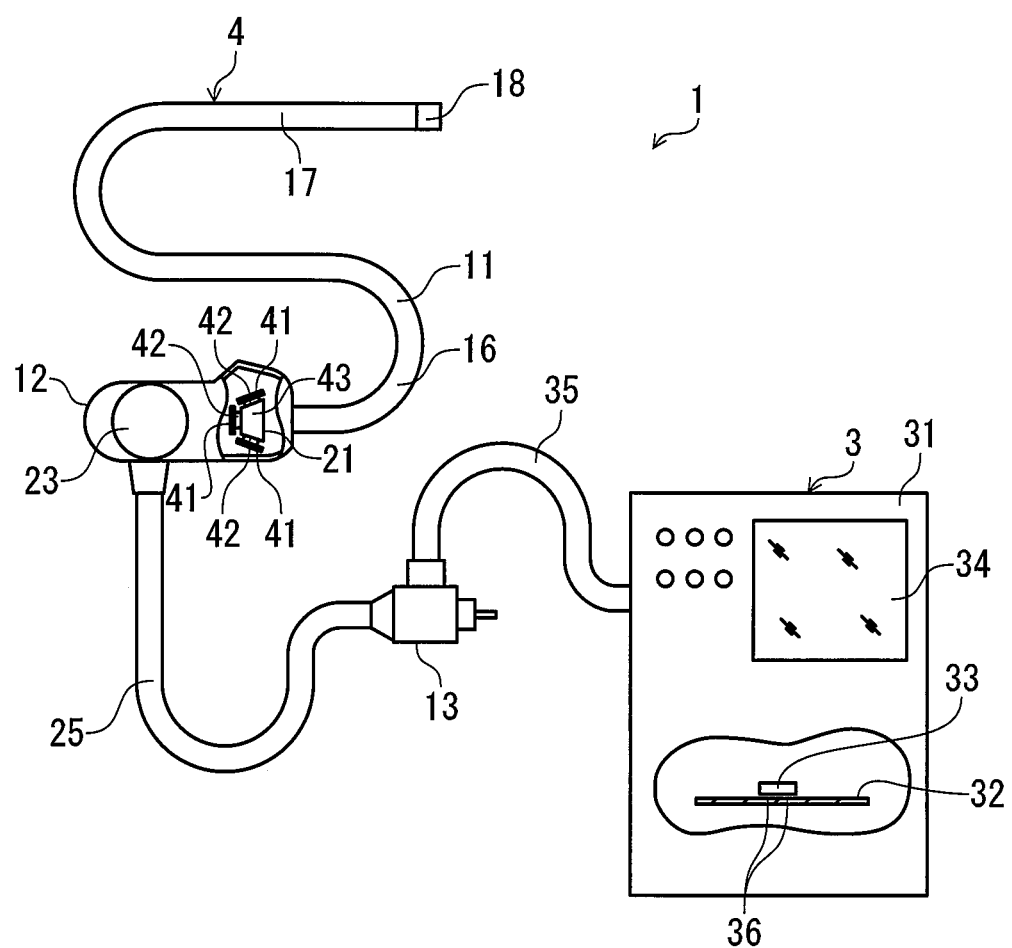
FIG. 1 is a front view schematically showing an endoscope apparatus according to a first embodiment.

Hereinafter, a first embodiment will be described with reference to FIGS. 1 to 11. FIG. 1 is a front view schematically showing an endoscope apparatus 1. The endoscope apparatus 1 is an example of electronic apparatuses.

As shown in FIG. 1, the endoscope apparatus 1 includes a main unit 3 and an endoscope 4. The main unit 3 is an example of a first part. The endoscope 4 is an example of a second part. The endoscope 4 includes an insertion unit 11, an operation unit 12, and a connection unit 13.

The insertion unit 11 is connected to the operation unit 12. The insertion unit 11 includes a tube 16, a movable unit 17, and an end unit 18. The tube 16 is a flexible tube that extends from the operation unit 12. The movable unit 17 has flexibility and is mounted so as to be continuously connected from the tube 16.

The end unit 18 is attached to a tip end of the movable unit 17. The end unit 18 has rigidity and is formed into a cylindrical shape. The end unit 18 is provided with a plurality of holes for photographing, lighting, and passing forceps therethrough and suctioning.

The operation unit 12 includes an imaging unit 21 and an operation knob 23. The operation unit 12 is provided with an insertion hole for inserting the forceps. The imaging unit 21 is embedded in the operation unit 12 and is connected to the end unit 18 of the insertion unit 11 via, for example, a glass fiber penetrating through the tube 16 and the movable unit 17. The imaging unit 21 captures videos that are seen from the holes of the end unit 18 to which the glass fiber is connected. The operation knob 23 warps the movable unit 17 of the insertion unit 11 via a wire penetrating through the tube 16.

The connection unit 13 is connected to the operation unit 12 via a connection tube 25. The connection unit 13 has various connectors that are connected to the main unit 3. Various cables or tubes are connected to the end unit 18 by penetrating through connection tube 25, the operation unit 12, the tube 16, and the movable unit 17 from the connection unit 13.

The main unit 3 includes a housing 31, a first board 32, a first electronic component 33, a monitor 34, and a connection cable 35. The first board 32 is an example of a first circuit board and the first board. The first electronic component 33 is an example of the first electronic component and a first component.

The housing 31 accommodates several components such as the first board 32, the first electronic component 33, the monitor 34, and a light source supplying illumination light. The first board 32 is a printed circuit board. The first electronic component 33 is a processor that controls the imaging unit 21 and processes video data captured by the imaging unit 21. The first electronic component 33 is electrically connected to the first board 32 via a first solder 36. In FIG. 1, the first solder 36 is schematically shown by a thick line. The first solder 36 is so-called lead free solder and includes, for example, tin, silver, and copper. Further, a composition of the first solder 36 is not limited thereto.

The monitor 34 is exposed from the housing 31 and displays the videos of the imaging unit 21 that are processed by the first electronic component 33. The connection cable 35 extends from the housing 31 and is connected to the connector of the connection unit 13 in the endoscope 4. The main unit 3 is connected to the operation unit 12 via the connection unit 13 to which the connection cable 35 is connected. The main unit 3 transfers signals between main unit 3 and endoscope 4 or supplies the illumination light, via the connection cable 35.

As shown in FIG. 1, the imaging unit 21 includes three second boards 41, three second electronic components 42, and a prism 43. The second board 41 is an example of a second circuit board and the second board. The second electronic component 42 is an example of the second electronic component and a second part.

Figure 2:
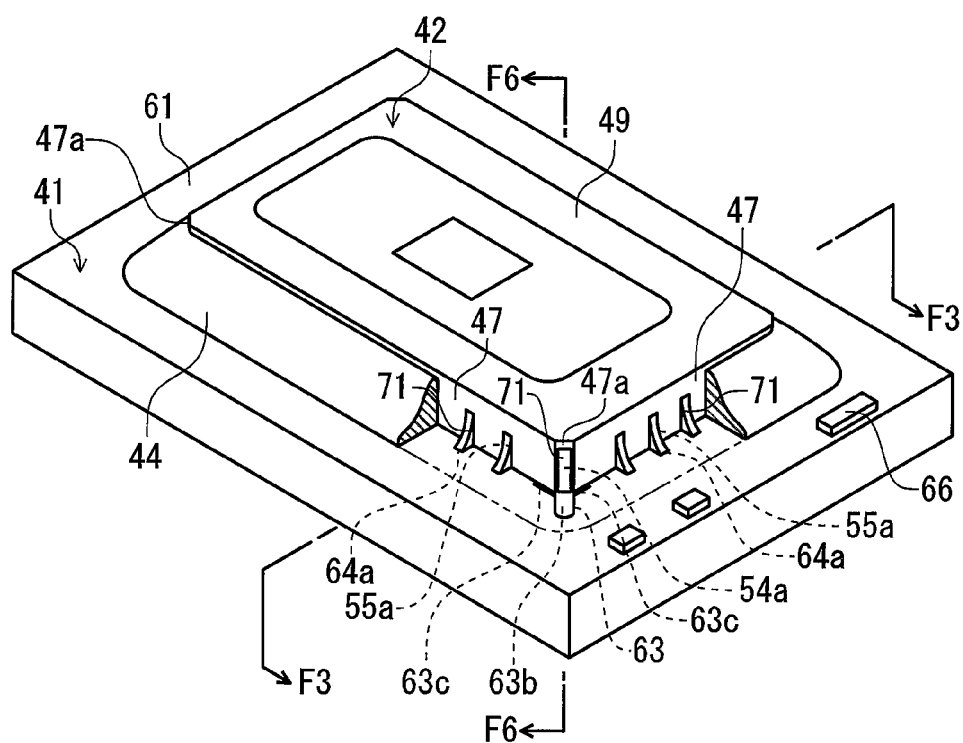
FIG. 2 is a perspective view showing a second electronic component mounted on a second board of the first embodiment.
Figure 3:
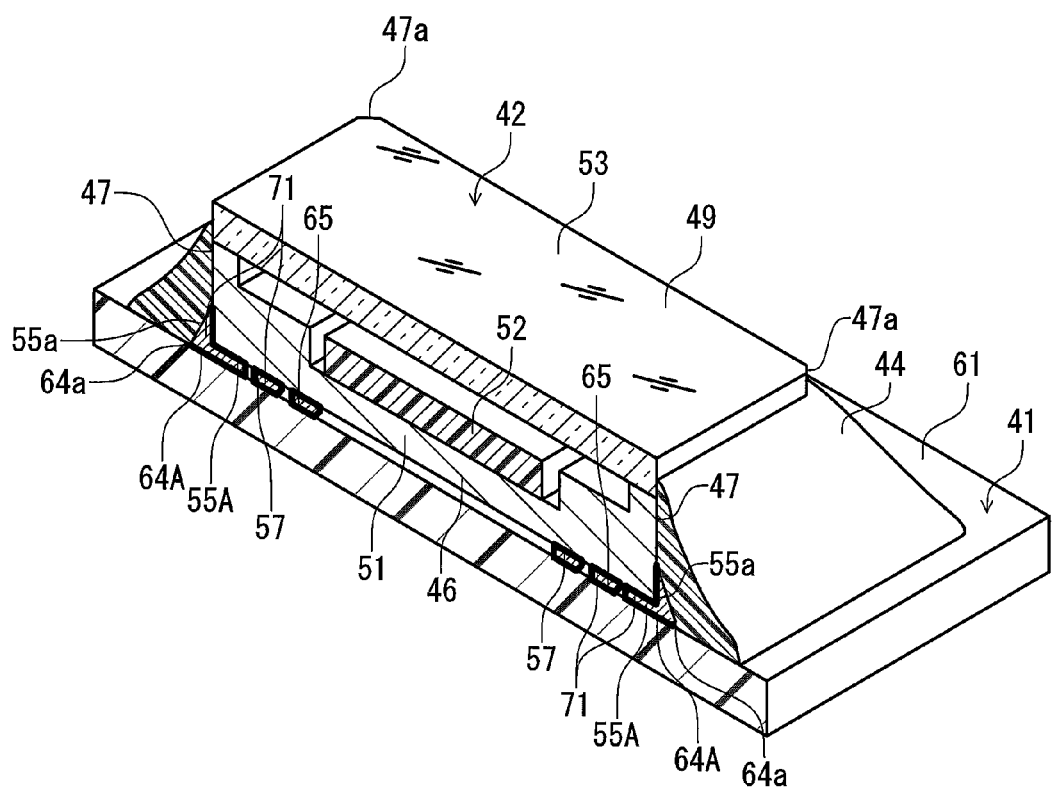
FIG. 3 is a cross-sectional perspective view showing the second electronic component, taken along line F3-F3 of FIG. 2.

FIG. 2 is a perspective view showing one of the second electronic components 42 mounted on one of the second boards 41. FIG. 3 is a cross-sectional perspective view showing the second electronic component 42 mounted on the second board 41, taken along line F3-F3 of FIG. 2.

Three second boards 41 and three second electronic components 42 each have the same configuration. For this reason, one of the second boards 41 and one of the second electronic components 42 will be representatively described below.

As shown in FIG. 2, the second electronic component 42 that is a CMOS sensor is mounted on the second board 41. A bonding member 44 is bonded to the second electronic component 42 and the second board 41.

The second electronic component 42 is an substantially rectangular land grid array (LGA) package. As partially shown in FIG. 3, the second electronic component 42 includes a bottom face 46, four lateral portions 47, and a top face 49.

The bottom face 46 faces the second board 41. Each of the four lateral portions 47 is raised from the bottom face 46. A corner portion 47a that is a portion of the lateral portion 47 is formed between the adjacent lateral portions 47. The corner portion 47a is an inclined surface by, for example, 45° from the lateral portions 47. The corner portion 47a is a chamfered portion, but is not limited thereto. Therefore, the corner portion 47a may be a ridge on which adjacent lateral portions 47 are formed. The top face 49 is disposed at an opposite side of the bottom face 46 and comes in contact with the prism 43.

As shown in FIG. 3, the second electronic component 42 includes a board 51, a chip 52, and a light transmitter 53.

The board 51 is formed by, for example, ceramic with a box shape of which the portion is opened. The board 51 has a lower linear expansion coefficient than that of the second board 41. The board 51 forms the bottom face 46 and the four lateral portions 47 of the second electronic component 42.

The chip 52 is accommodated in the board 51 and, for example, converts received optical information into data. The light transmitter 53 is, for example, a transparent glass plate and covers an opening part of the board 51. The light transmitter 53 forms the top face 49 of the second electronic component 42.

Figure 4:
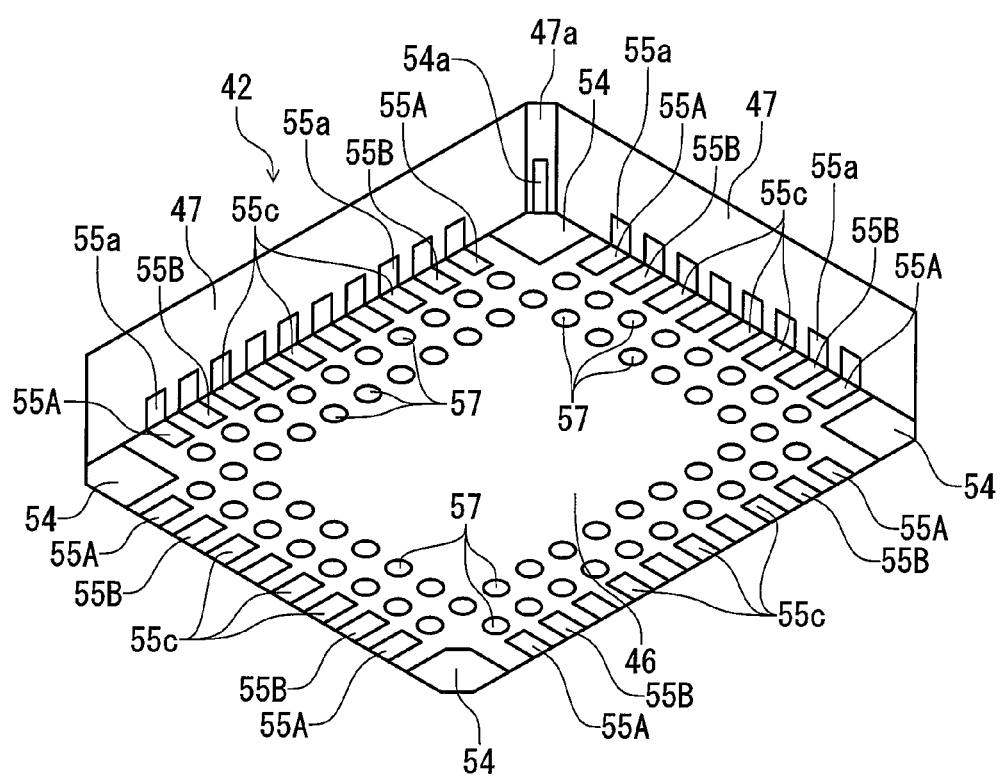
FIG. 4 is a perspective view showing a bottom face of the second electronic component.

FIG. 4 is a perspective view showing the bottom face 46 of the second electronic component 42. As shown in FIG. 4, the second electronic component 42 is provided with a plurality of first outer electrodes 54, a plurality of second outer electrodes 55A, 55B, and 55C, and a plurality of first inner electrodes 57. Each of the first outer electrodes 54 is an example of a first electrode and another electrode. The second outer electrode 55A is an example of a second electrode. The second outer electrode 55B is an example of a fifth electrode. Each of the first outer electrodes 54, the second outer electrodes 55A, 55B, and 55C, and the first inner electrodes 57 are electrically connected to the chip 52.

Each of the first outer electrodes 54 is provided on each of the corner portions of the bottom face 46 and is formed into a substantially rectangular shape. Each of the corner portions of the bottom face 46 is a part which contacts two lateral portions 47 and one corner portion 47a. Further, the first outer electrodes 54 contact the edges of the bottom face 46, respectively, and may be spaced apart from the edge of the bottom face 46.

Each of the first outer electrodes 54 has a side electrode 54a. The side electrode 54a is formed into a rectangular shape and extends to the corner portion 47a. That is, each of the first outer electrodes 54 is provided across the corner portions of the bottom face 46 and the corner portion 47a.

The second outer electrodes 55A, 55B, and 55C are respectively mounted so as to abut the edges of the bottom face 46. The edges of the bottom face 46 are portions abutting the lateral portions 47. Each of the second outer electrodes 55A, 55B, and 55C have a side electrode 55a. The side electrode 55a is formed into a rectangular shape and extends to the lateral portion 47. That is, each of the second outer electrodes 55A, 55B, and 55C is provided across the bottom face 46 and the lateral portion 47.

Each of the second outer electrodes 55A is provided so as to be adjacent to each of the first outer electrodes 54. Each of the second outer electrodes 55B is provided so as to be adjacent to each of the second outer electrodes 55A. The second outer electrodes 55C are arranged between one of the second outer electrodes 55B and other one of the second outer electrodes 55B.

Each of the first inner electrodes 57 is formed into a circular shape. The first inner electrodes 57 are mounted so as to be surrounded by the first outer electrodes 54, and the second outer electrodes 55A, 55B, and 55C. The first inner electrodes 57 are arranged in two rows along the second outer electrodes 55A, 55B, and 55C.

Figure 5:
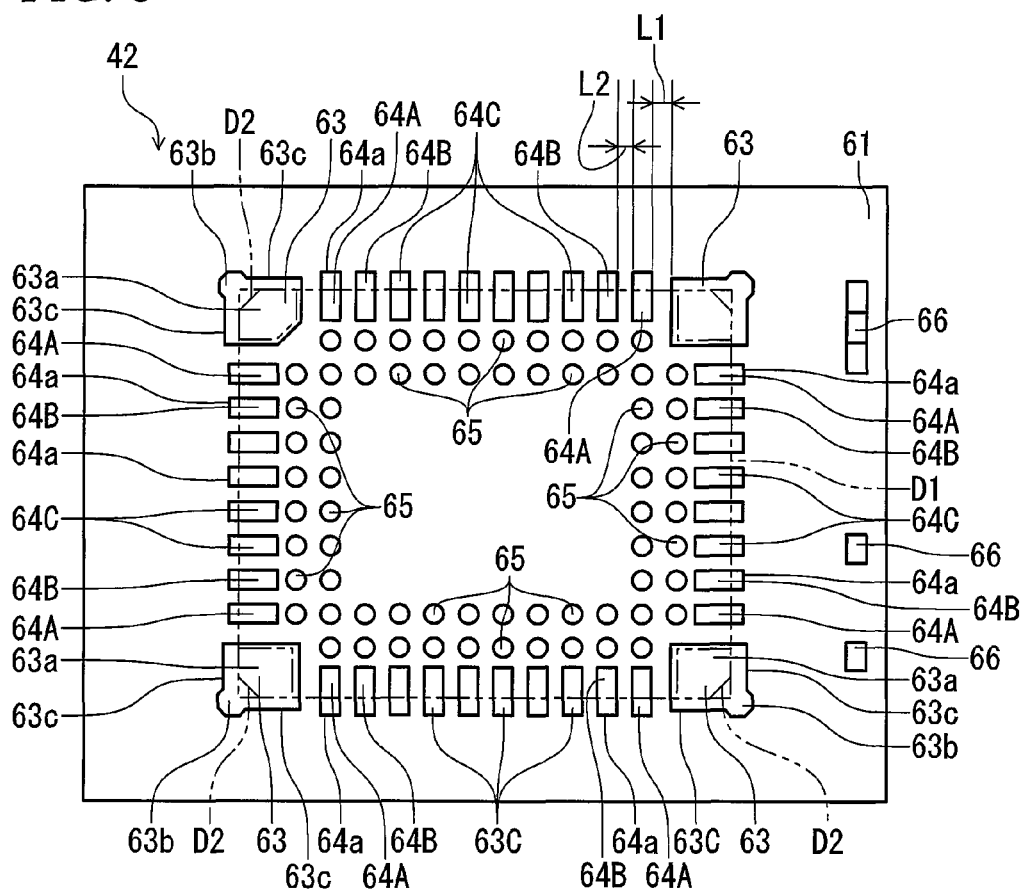
FIG. 5 is a plan view showing the second board.

FIG. 5 is a plan view showing the second board 41. The second board 41 is a printed circuit board and is formed of, for example, a heat-resistant glass fabric substrate epoxy resin copper clad laminate (FR-4). The second board 41 has a mounting surface 61 facing the second electronic component 42. The mounting surface 61 includes a first area D1 covered with the second electronic component 42 and second areas D2 facing each of the first outer electrodes 54. In several drawings, the first area D1 and the second areas D2 are respectively shown by two-dot chain lines.

As shown in FIG. 5, the mounting surface 61 is provided with a plurality of third outer electrodes 63, a plurality of fourth outer electrodes 64A, 64B, and 64C, a plurality of second inner electrodes 65, and a plurality of components 66. Each of the third outer electrodes 63 is an example of a third electrode and electrodes. Each of the fourth outer electrodes 64A is an example of a fourth electrode. Each of the fourth outer electrodes 64B is an example of a sixth electrode.

Each of the third outer electrodes 63 is mounted so as to correspond to each of the first outer electrodes 54 of the second electronic component 42. Each of the third outer electrode 63 includes a first electrode portion 63a and a second electrode portion 63b.

Each of the first electrode portion 63a faces each of the first outer electrodes 54 of the second electronic component 42, and, is formed into an rectangular shape. The first electrode portion 63a is formed to have a wider area than that of corresponding first outer electrode 54. The first electrode portion 63a has a pair of edges 63c along each of the lateral portions 47 of the second electronic component 42. The edge 63c is located outside of the first area D1. Further, a part of the first electrode portion 63a is located outside of the second area D2 in the first area D1. A part of the first electrode portion 63a is a portion that faces each of the fourth outer electrode 64A. The distance between each of the third outer electrodes 63 and each of the fourth outer electrodes 64A is shorter than the distance between each of the first outer electrodes 54 and each of the second outer electrodes 55A of the second electronic component 42.

Each of the second electrode portions 63b is continuously formed from the first electrode portion 63a. The second electrode portion 63b extends in a direction to which the side electrode 54a of the first outer electrode 54 proceeds from a position corresponding to the corner portion 47a of the second electronic component 42. For example, the second electrode portion 63b extends in a direction orthogonal to the corner portion 47a. The width of each of the second electrode portions 63b is wider than that of the side electrode 54a of the first outer electrode 54.

Each of the fourth outer electrodes 64A faces each of the second outer electrodes 54 of the second electronic component 42. Each of the fourth outer electrodes 64A is mounted so as to be adjacent to each of the third outer electrodes 63. Each of the fourth outer electrodes 64B faces each of the second outer electrodes 55B. Each of the fourth outer electrodes 64B is mounted so as to be adjacent to each of the fourth outer electrodes 64A. Each of the fourth outer electrodes 64C faces each of the second outer electrodes 55C. The fourth outer electrode 64C is arranged between one of the fourth outer electrodes 64B and other one of the fourth outer electrodes 64B.

The fourth outer electrodes 64A, 64B, and 64C are respectively formed into an substantially same rectangular shape. The fourth outer electrodes 64A, 64B, and 64C are formed to have a wider area than that of corresponding second outer electrodes 55A, 55B, and 55C. Each of the fourth outer electrodes 64A, 64B, and 64C have an edge 64a along the lateral portions 47 of second electronic component 42. The edge 64a is located outside of the first area D1. As shown in FIG. 5, a distance L1 between the third outer electrode 63 and the second outer electrode 64A is longer than a distance L2 between the second outer electrode 64A and the second outer electrode 64B.

The second inner electrodes 65 are respectively formed into a circular shape, corresponding to the first inner electrodes 57 of the second electronic component 42. The second inner electrodes 65 are provided so as to be surrounded by the third outer electrodes 63 and the fourth outer electrodes 64A, 64B, and 64C. The second inner electrodes 65 are arranged in two rows along the fourth outer electrodes 64A, 64B, and 65C.

Figure 6:
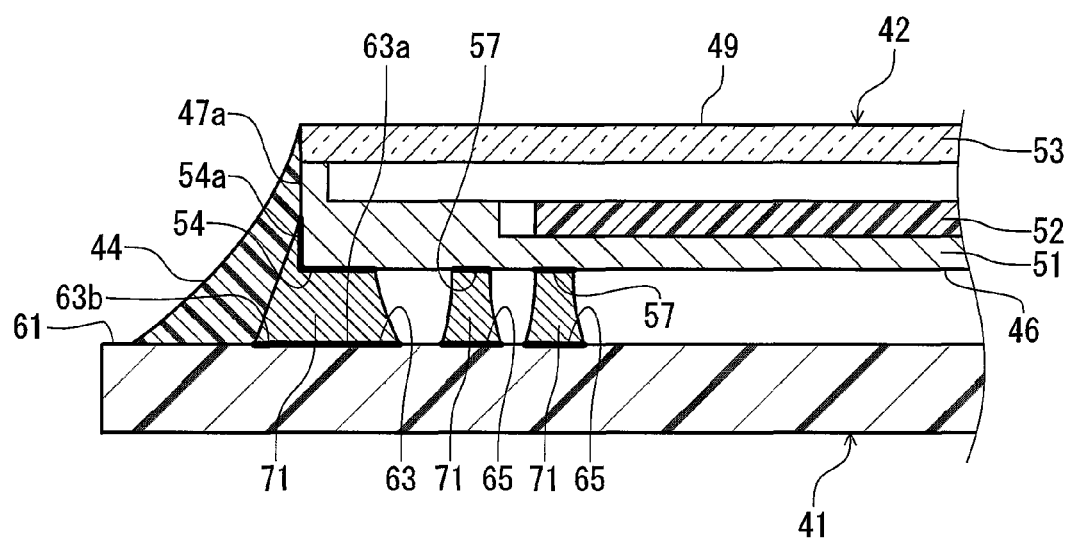
FIG. 6 is a cross-sectional view showing the second electronic component, taken along line F6-F6 of FIG. 2.

FIG. 6 is a cross-sectional view showing the second electronic component 42 mounted on the second board 41 taken along line F6-F6 of FIG. 2. For the convenience of explanation, some part such as a second solder 71 is shown in FIG. 6 with a magnified view.

As shown in FIG. 6, the third outer electrode 63 of the second board 41 is soldered to the first outer electrode 54 of second electronic component 42. That is, the third outer electrode 63 is electrically connected to the first outer electrode 54 by the second solder 71. The second solder 71 is bonded to the first outer electrode 54 including the side electrode 54a and the third outer electrode 63.

The second solder 71 forms a soldering fillet across the side electrode 54a of the first outer electrode 54 and the second electrode part 63b of the third outer electrode 63. Further, the second solder 71 forms a soldering fillet across the outer edge of the first outer electrode 54 and the edge 63c of the third outer electrode 63 that is located outside of the first area D1. In addition, the second solder 71 forms a soldering fillet across the inner edge of the first outer electrode 54 and the inner edge of the third outer electrode 63 that is located outside of the second area D2. Note that the inner edge of the first outer electrode 54 faces the second outer electrode 55A, and that the inner edge of the third outer electrode 63 faces the fourth outer electrode 64A.

As partially shown in FIG. 3, the fourth outer electrodes 64A, 64B, and 64C are soldered to corresponding second outer electrodes 55A, 55B, and 55C. That is, the fourth outer electrodes 64A, 64B, and 64C are electrically connected to the second outer electrodes 55A, 55B, and 55C by the second solders 71, respectively. The second solders 71 are respectively bonded to the second outer electrodes 55A, 55B, and 55C including the side electrodes 55a and the fourth outer electrodes 64A, 64B, and 64C.

The second solder 71 forms a soldering fillet across the side electrodes 55a of the second outer electrodes 55A, 55B, and 55C and the edges 64a of the fourth outer electrodes 64A, 64B, and 64C that are located outside of the first area D1.

Each of the first inner electrodes 57 is soldered to corresponding second inner electrode 65. That is, each of the first inner electrodes 57 is electrically connected to each of the second inner electrodes 65 by the second solder 71. The second solder 71 forms a soldering fillet across the edge of the first inner electrode 57 and the edge of the second inner electrode 65.

As described above, the second electronic component 42 is electrically connected to the second board 41 by the second solder 71.

The second solder 71 is so-called a high-reliability solder including, for example, tin, silver, copper, bismuth, antimony, and nickel. Further, the composition of the second solder 71 is not limited thereto. The second solder 71 also has higher stress resistance than that of the first solder 36. For example, the second solder 71 is rigid and is difficult to extend as compared with the first solder 36. In addition, the second solder 71 is difficult to be deformed and has a long creep lifespan. Moreover, the second solder 71 has a melting point and viscosity higher than that of the first solder 36.

Bismuth and antimony are examples of V-group elements. The solder to which the bismuth is added has increased flowability and decreased melting point. The solder to which the antimony is added becomes more rigid and has an increased melting point. The solder to which the nickel is added makes the bonding between metals tighter and suppresses solidification cracking.

As shown in FIG. 2, the bonding member 44 is bonded to the lateral portions 47 of the second electronic component 42 and the mounting surface 61 of the second board 41. Further, in FIG. 2, the bonding member 44 is shown by being partially cut. The bonding member 44 is bonded to the second electronic component 42 throughout the entire circumference of the lateral portions 47.

The bonding member 44 is a thermosetting epoxy resin in which a filler such as silica is mixed. For example, 75 wt % of the filler is mixed in the bonding member 44. The bonding member 44 is hardened at, for example, 120° C. The bonding member 44 has a low linear expansion coefficient and a small change in a physical property at high temperature.

The bonding member 44 has a glass transition point higher than that of the second board 41. For example, the glass transition point of the bonding member 44 is 160° C. and the glass transition point of the second board 41 is 140° C.

The bonding member 44 has high viscosity and is difficult to be widened. For this reason, the bonding member 44 is bonded to the lateral portions 47 up to the position close to the top face 49 of the second electronic component 42.

Figure 7:
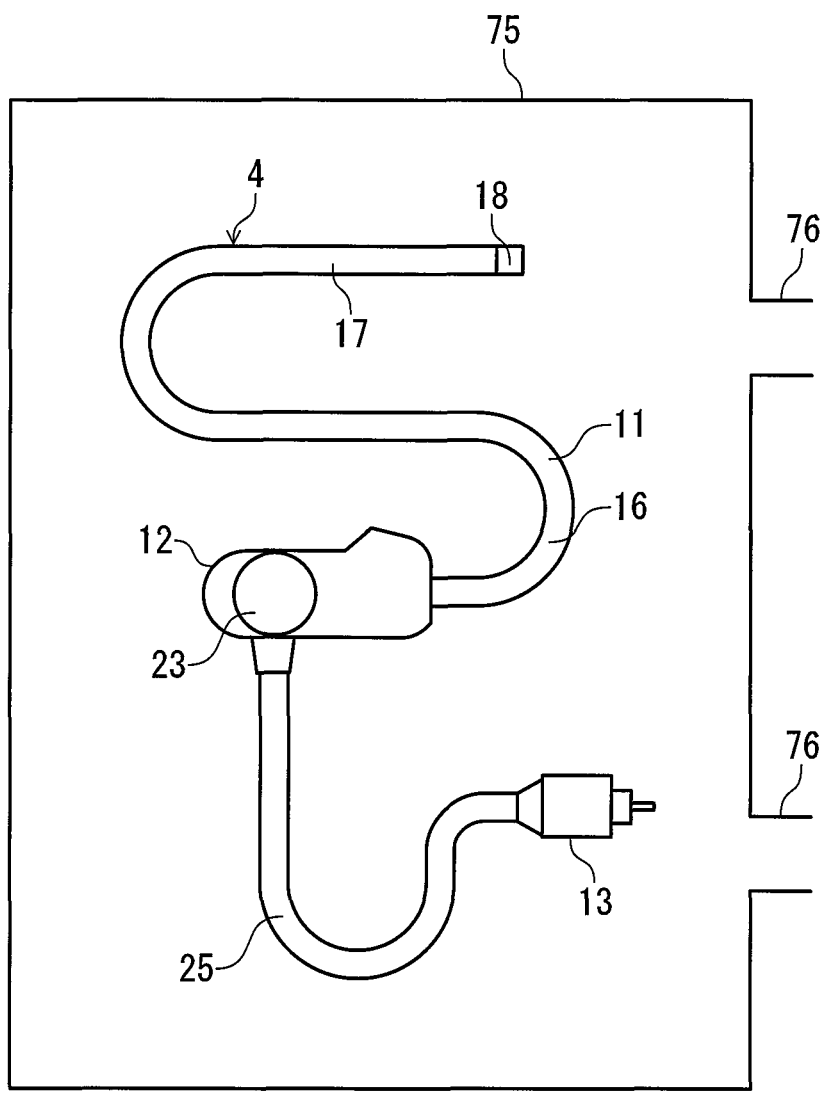
FIG. 7 is a plan view schematically showing an endoscope housed in a case of the first embodiment.

FIG. 7 is a plan view schematically showing the endoscope 4 accommodated in the case 75. The endoscope 4 is subjected to the boiling disinfection by the autoclave device so as to be sterilized. Hereinafter, the sequence of the boiling disinfection of the endoscope 4 having the above-mentioned configuration is schematically described.

First, the connection cable 35 is separated from connection unit 13 of the endoscope 4 and the connector of the connection unit 13 is covered with, for example, a cap. Next, the endoscope 4 is accommodated in the case 75. The case 75 includes a tray in which the endoscope 4 is disposed and a cover covering the tray. The case 75 is provided with a plurality of vent holes 76 that guide high pressure steam.

Next, the case 75 is disposed in a sterilizing chamber of the autoclave device and the sterilizing chamber is sealed. First, the autoclave device makes pressure in the sterilizing chamber lower than atmospheric pressure. Next, the autoclave device supplies the high pressure steam to the sterilizing chamber. The high pressure steam is introduced into the case 75 from the vent holes 76, such that the inside of the case 75 is pressurized and heated. For example, the sterilizing chamber is being maintained at 138° C. for 5 minutes and is in a 2 atmospheric pressure status. Thereby, the endoscope 4 accommodated in case 75 is disinfected by boiling.

Further, a boiling disinfection method repeating a supply and exhaust of high pressure steam is known. For example, the sterilizing chamber is made to be in a high temperature and high pressure state, and then, the steam is exhausted from the sterilizing chamber. Thereby, the temperature in the sterilizing chamber falls to room temperature and the pressure in the sterilizing chamber also falls to atmospheric pressure. The supply and exhaust of high pressure steam is repeated, for example, three times, such that the endoscope 4 is more surely disinfected than normal boiling disinfection method. In other words, the endoscope 4 is disinfected with being repeatedly undergone the rising and falling of temperature between the first temperature that is 138° C. and the second temperature that is the room temperature. However, the first temperature and the second temperature are not limited thereto.

The plurality of components 66 are various electronic components such as a capacitor. The plurality of components 66 are respectively mounted on the second board 41. The plurality of components 66 are disposed so as to be spaced apart from each other from a position at which the second electronic component 42 and the bonding member 44 are disposed.

Figure 8:
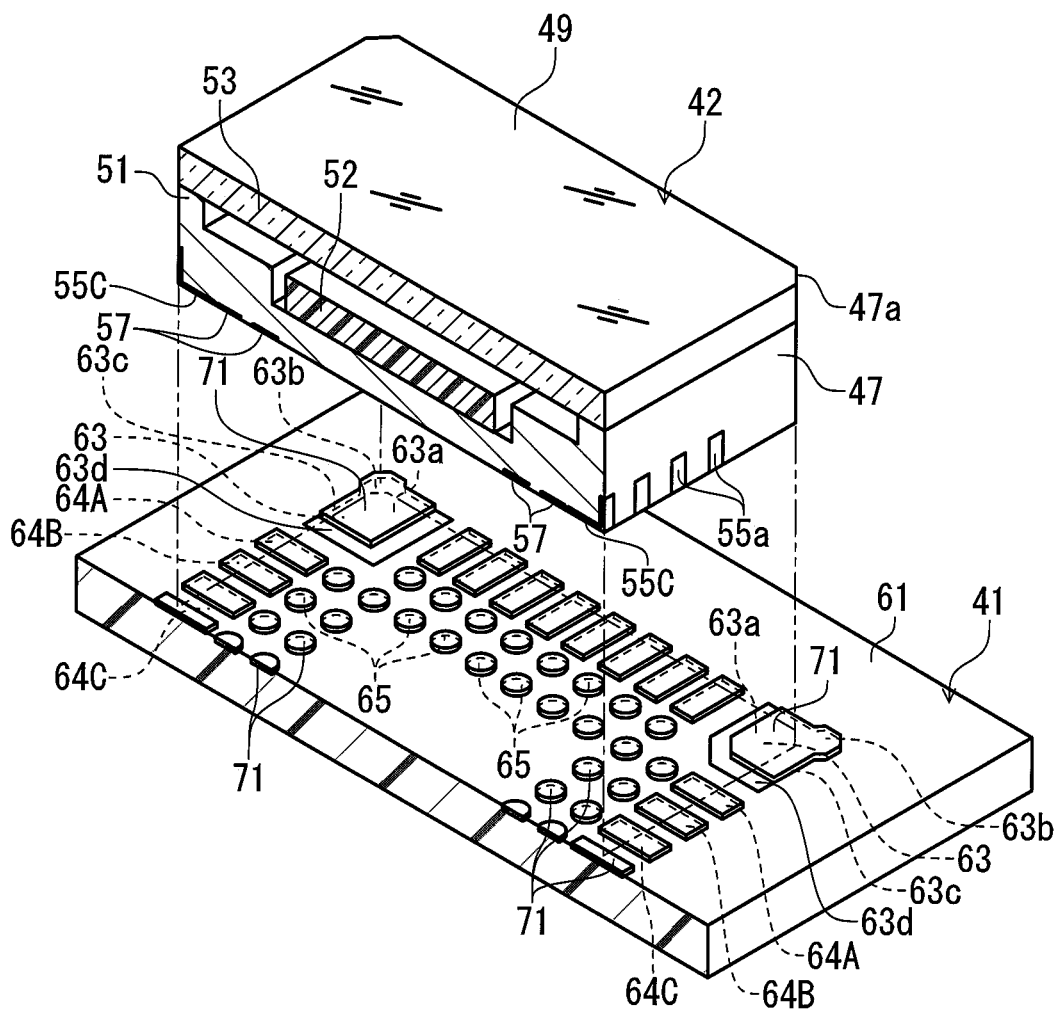
FIG. 8 is a perspective view showing the second board and the second electronic component in a manufacturing process of the first embodiment.
Figure 9:
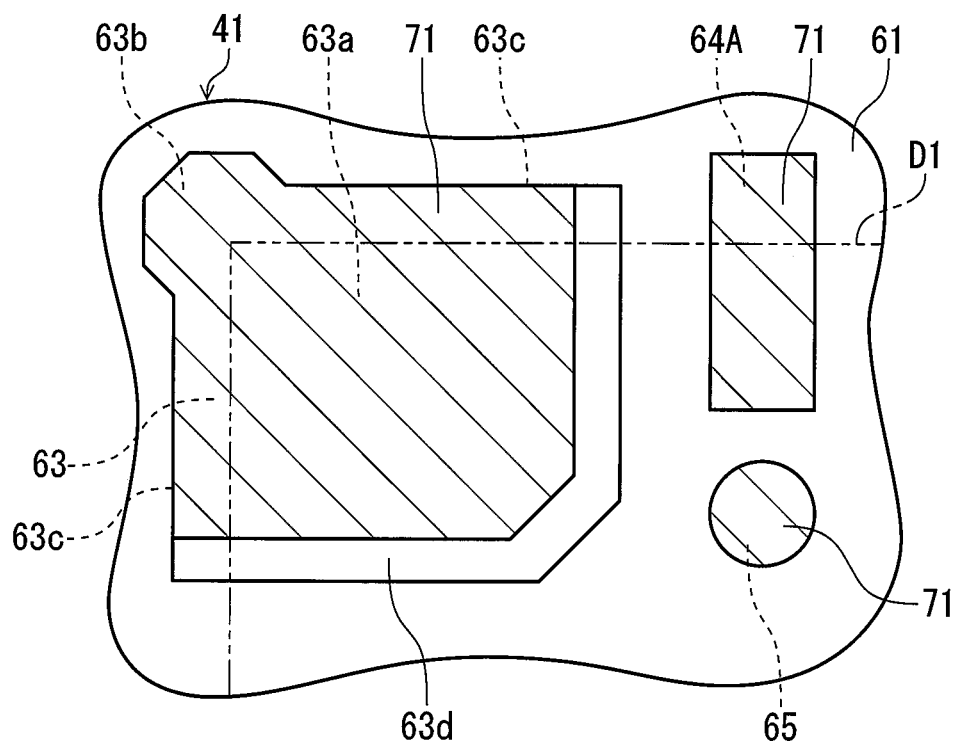
FIG. 9 is an enlarged plan view of a third outer electrode of the first embodiment.

FIG. 8 is a perspective view showing the second board 41 and the second electronic component 42 during a manufacturing process. FIG. 9 is an enlarged plan view showing one of the third outer electrodes 63. An example of a method of mounting the second electronic component 42 that is a portion of the method of manufacturing the endoscope apparatus 1 having the above-mentioned configuration will be described with reference to FIGS. 8 and 9.

First, as shown in FIG. 8, the paste-like second solder 71 is applied to each of the third outer electrodes 63, the fourth outer electrodes 64A, 64B, and 64C, and the second inner electrodes 65 before the second electronic component 42 is mounted. The second solder 71 is applied to each of the electrodes 63, 64A, 64B, 64C, and 65, for example, in a printing process that uses a metal mask. The amount of the second solder 71 to be applied to an area of each of the electrodes 63, 64A, 64B, 64C, and 65 is smaller than the amount of first solder 36, which bonds the first board 32 and the first electronic component 33 of the main unit 3, to be applied to each electrode area.

As shown in FIG. 9, the second solder 71 is applied to each of the third outer electrodes 63 so that a portion 63d of the third outer electrode 63 is exposed. The exposed portion 63d of the third outer electrode 63 is an appropriate L-letter shape portion along the inner edge of the third outer electrode 63. The exposed portion 63d is disposed so as to be sandwiched between the second solder 71 and the fourth outer electrode 64A.

The exposed portion 63d is formed by making an opening formed on the metal mask smaller than the third outer electrode 63. That is, the second solder 71 is printed in a state in which the second solder 71 covers the portion 63d where the metal mask is exposed.

Next, as shown in FIG. 8, the second electronic component 42 is disposed on the second board 41. In this case, each of second solders 71 is bonded to the third outer electrodes 63, the fourth outer electrodes 64A, 64B, and 64C, and the second inner electrodes 65, respectively.

The second electronic component 42 that is disposed is pressed toward second board 41 by a jig such as a plate spring. In this state, the second electronic component 42 and the second board 41 are put in a reflow furnace so as to be heated. Thereby, the second solder is melted so that each of the electrodes 54, 55A, 55B, 55C, and 57 of the second electronic component 42 is soldered to each of the electrodes 63, 64A, 64B, 64C, and 65 of the second board 41.

In the above-mentioned reflow process, the second electronic component 42 is pressed toward the second printed circuit board, such that the second solder 71 is collapsed. Collapsed second solder 71 is widened toward a lateral direction.

The second solder 71 applied to each of the third outer electrodes 63 flows by the pressing force and covers the portion 63d where the third outer electrode is exposed. The second solder 71 is further widened by the pressing force. Since the bonding area of the second solder 71 and the third outer electrode 63 is large, the excessive widening of the second solder 71 is suppressed and the separation of a soldering ball from the second solder 71 is suppressed.

The third outer electrode 63 to which a large amount of the second solder 71 is applied is farther spaced apart from the fourth outer electrode 64A than the distance between the fourth outer electrodes 64A and 64B. For this reason, the short-circuiting of the third outer electrode 63 and the fourth outer electrode 64A due to the widened second solder 71 is suppressed.

Next, the bonding member 44 is applied to the second electronic component 42 and the second board 41 on which the second solder 71 is cured. Non-cured bonding member 44 is applied across the lateral portions 47 of the second electronic component 42 and the mounting surface 61 of the second board 41 by a dispenser. The bonding member 44 is applied throughout the entire circumference of the lateral portions 47 of the second electronic component 42. A gap between the second electronic component 42 and the second board 41 is sealed by the bonding member 44.

Next, the second electronic component 42 and the second board 41 are put in the hardening furnace. The hardening furnace heats the bonding member 44, for example, at 120° C. for 30 minutes. Thereby, the bonding member 44 is hardened.

By the above process, the second electronic component 42 is mounted on the second board 41.

According to the endoscope apparatus 1 having the above configuration, each of the electrodes 63, 64A, 64B, 64C, and 65 of the second board 41 is electrically connected to each of the electrodes 54, 55A, 55B, 55C, and 57 of the second electronic component 42 by the second solder 71. Since the linear expansion coefficients of the board 51 of the second electronic component 42 and the second board 41 are different from each other, a load may be applied to the second solder 71. However, the second solder 71 has higher stress resistance than that of the first solder 36 used in the main unit 3. For this reason, even though the endoscope 4 is heated by the autoclave device, the deterioration of the second solder 71 may be suppressed.

The bonding member 44 bonds the second electronic component 42 to the second board 41 and fixes the second electronic component 42 to the second board 41. The bonding member 44 has the glass transition point higher than that of the second board 41. For this reason, even though the endoscope 4 is heated by the autoclave device, the change in characteristics of the bonding member 44 is negligible, thereby rigidly fixing the second electronic component 42 to the second board 41. Therefore, the load generated by the difference in the linear expansion coefficients between the board 51 of the second electronic component 42 and the second board 41 may be reduced and thus, the deterioration of the second solder 71 may be suppressed. For example, the occurrence of the cracking in the second solder 71 may be delayed.

As described above, deterioration due to the boiling disinfection of the second solder 71 may be suppressed by using the second solder 71 and the bonding member 44 which have a high stress resistance.

Each of the electrodes 63, 64A, 64B, 64C, and 65 of the second board 41 is formed to have an area larger than that of each of the electrodes 54, 55A, 55B, 55C, and 57 of the second electronic component 42. For this reason, the soldering fillet of the second solder 71 is clearly formed. Further, a cross sectional area of the second solder 71 is increased to improve the stress resistance of the second solder 71, thereby suppressing the deterioration of the second solder 71. In addition, the amount of the second solder 71 to be applied may be easily adjusted and thus, it becomes easy to apply the second solder 71.

The amount of the second solder 71 to be applied to each electrode area is smaller than the amount of the first solder 36 to be applied to each electrode area. For this reason, the volume variation of the second solder 71 due to heating is smaller than that of the first solder 36. As a result, the load that may be applied to the second solder 71 due to the volume variation accompanied by the rising and falling of temperature and the deterioration of the second solder 71 may be suppressed.

The amount of the second solder 71 to be applied to each electrode area may be larger than the amount of the first solder 36 to be applied to each electrode area. In this case, the second solder 71 is expanded and contracted, such that the load applied due to the rising and falling of temperature is mitigated. Thereby, the deterioration of the second solder 71 may be suppressed.

The second electronic component 42 that is the LGA package has a small gap between the second electronic component 42 and the second board 41 and is difficult to be subjected to an underfilling by a flux. Meanwhile, the bonding member 44 is bonded to the lateral portions 47 of the second electronic component 42. As described above, even though the gap between the second electronic component 42 and the second board 41 is narrow, the second electronic component 42 may be rigidly fixed to the second board 41.

The bonding member 44 is applied throughout the entire circumference of the lateral portions 47 of the second electronic component 42 to seal the gap between the second electronic component 42 and the second board 41. Thereby, the flowing out of the flux from the gap between the second electronic component 42 and the second board 41 may be prevented.

The plurality of components 66 are disposed so as to be spaced apart from the position at which the second electronic component 42 and the bonding member 44 are disposed. Thereby, the application of the bonding member 44 is facilitated by the dispenser, thereby improving the manufacturing efficiency of endoscope 4.

Each of the edges 63c of the third outer electrodes 63 is out of the first area D1 and has a wider area than that of each of the first outer electrodes 54. For this reason, the area in which the second solder 71 may be bonded and the flowing of the second solder 71 is absorbed is formed to be widened. Thereby, the excessive widening of the second solder 71 is suppressed when the second solder 71 is mounted and the separation of the soldering ball from the second solder 71 is suppressed. Thereby, the short-circuiting caused by the soldering ball is suppressed.

Each of the edges 63c of the third outer electrodes 63 is located outside of the first area D1. In other words, each of the third outer electrodes 63 protrudes outwardly from the first area D1. For this reason, even though the area of the third outer electrode 63 is wider than the first outer electrode 54, the short-circuiting of the third outer electrode 63 and the fourth outer electrode 64A near the electrode 63 may be suppressed. The manufacturing efficiency of the endoscope apparatus 1 is improved through the suppression of the short-circuiting.

The amount of the second solder 71 applied to the third outer electrode 63 is larger than that of the second solder 71 applied to each of the fourth outer electrodes 64A, 64B, and 64C. Distance L1 between the third outer electrode 63 and the fourth outer electrode 64A is longer than distance L2 between the fourth outer electrodes 64A and 64B. Thereby, the second solder 71 applied to the third outer electrode 63 at the time of mounting is widened by the pressing to suppress the short-circuiting with the second solder 71 applied to the fourth outer electrode 64.

The width of the second electrode part 63b of the third outer electrode 63 is wider than that of the side electrode 54a of the first outer electrode 54. Thereby, the excessive widening of the second solder 71 applied to the second electrode part 63b at the time of mounting is suppressed and the short-circuiting due to the soldering ball is suppressed.

A portion of the first electrode part 63a of the third outer electrode 63 is located outside of the second area D2. For this reason, the second solder 71 forms the soldering fillet across the inner edge of the first outer electrode 54 and the inner edge of the third outer electrode 63. Thereby, the cross-sectional area of the second solder 71 becomes large, such that the deterioration of the second solder 71 may be suppressed.

The second solder 71 before the second electronic component 42 is mounted is applied to the third outer electrode 63 so as to expose a portion 63d of the third outer electrode 63. At the time of mounting, the second solder 71 applied to the third outer electrode 63 flows by the pressing force and covers the portion 63d where the third outer electrode is exposed. Thereby, the excessive widening of the second solder 71 applied to the third outer electrode 63 is suppressed and the short-circuiting caused by the soldering ball is suppressed.

The first embodiment is an example of the endoscope apparatus 1 and several components may be modified. Hereinafter, several modified examples will be described.

In the first embodiment, the imaging unit 21 is accommodated in the operation unit 12, but the imaging unit may be mounted at, for example, the end part 18 of the insertion unit 11.

In the first embodiment, the second electronic component 42 is the LGA package, but other kinds of electronic components such as a quad flat non-leaded (QFN) package may be employed as well.

In the first embodiment, the second solder 71 contains tin, silver, copper, bismuth, antimony, and nickel. However, the second solder 71 may be a solder containing, for example, germanium, indium, at least any one of other V-group elements. The solder including at least one of germanium and indium may be difficult to be cracked and may have the high stress resistance.

In the first embodiment, even though the second board 41 is formed by the FR-4, the second board 41 may be made of ceramic that is the same kind of material as the board 51 of the second electronic component 42. Thereby, the difference in the linear expansion coefficients between the second board 41 and the second electronic component 42 becomes small and thus, the deterioration of the second solder 71 may be suppressed.

The second board 41 may be formed to be thinner than the first board 32. The second board 41 is thinly formed, such that the second board 41 becomes easy to deform and the load according to the second solder 71 is reduced. Thereby, the deterioration of the second solder 71 may be suppressed.

Figure 10:
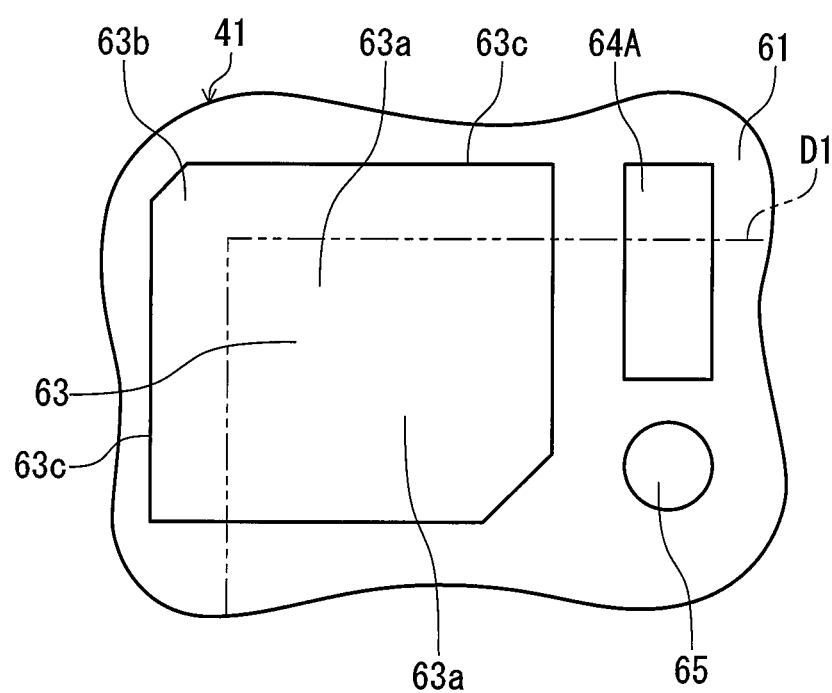
FIG. 10 is a plan view showing a modified example of the third outer electrode of the first embodiment.

FIG. 10 is a perspective view showing a modified example of the third outer electrode 63. As shown in FIG. 10, the edge 63c of the third outer electrode 63 may be spayed apart from the first area D1, as compared with the first embodiment. Further, the first electrode part 63a and the second electrode part 63b of the third outer electrode 63 may be integrally formed.

Figure 11:
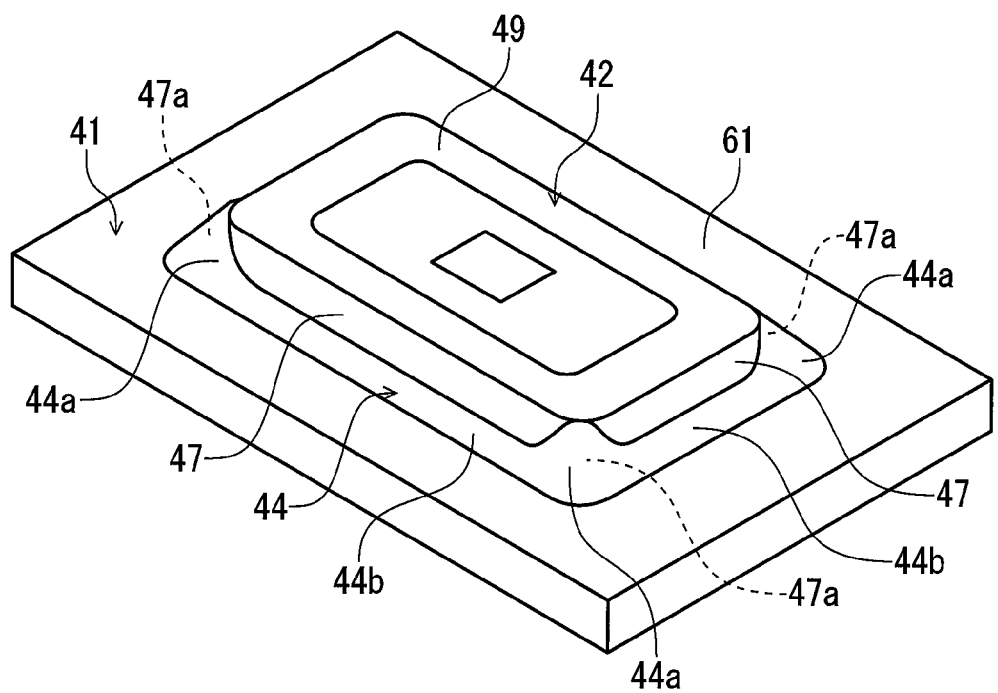
FIG. 11 is a perspective view showing a modified example of a bonding member of the first embodiment.

FIG. 11 is a perspective view showing a modified example of the bonding member 44. As shown in FIG. 11, the bonding member 44 may include a plurality of first application portions 44a and a plurality of second application portions 44b. The first application portion 44a is a portion bonded to the lateral portions 47 up to near the surface of the second electronic component 42. The second application portion 44b is a portion bonded to the lateral portions 47 around a middle portion in a height direction of the lateral portions. In other words, the amount of the resin of the first application portion 44a to be applied is larger than that of the resin of the second application portion 44b.

The first application portion 44a is bonded to the corner portions 47a of the second electronic component 42 and the lateral portions 47 near the corner portions 47a. In other words, the first application portion 44a is bonded to the corners of the second electronic component 42. The second application portion 44b is provided between the first application portions 44a.

The corners of the second electronic component 42 are easily concentrated with stress. For this reason, the first application portion 44a having a large amount of resin to be applied is provided at the corners of the second electronic component 42, thereby rigidly fixing the second electronic component 42 to the second board 41. Thereby, the deterioration of the second solder 71 may be suppressed. Further, the resin applied to a portion on which stress is difficult to be concentrated may be reduced, thereby reducing the manufacturing costs of the endoscope apparatus 1.

Figure 12:
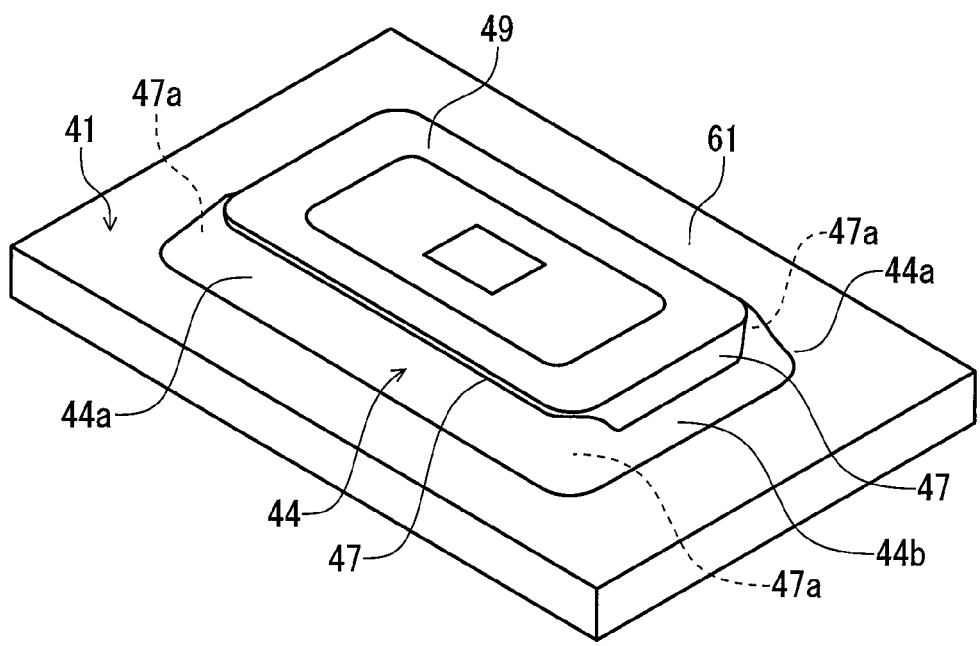
FIG. 12 is a perspective view showing another modified example of the bonding member of the first embodiment.

FIG. 12 is a perspective view showing another modified example of the bonding member 44. As shown in FIG. 12, the first application portion 44a may be mounted along a longer side of the second electronic component 42 and the second application portion 44b may be mounted along a shorter side of the second electronic component 42. That is, the amount of the bonding member 44 to be applied for the longer side and the shorter side of the second electronic component 42 may be different from each other. In other words, the cross-sectional shape of the bonding member 44 for the longer side and the shorter side of the second electronic component 42 may be different from each other.

The longer side of the second electronic component 42 is easily concentrated with stress. For this reason, the first application portion 44a having a large amount of resin to be applied is provided at the longer side of the second electronic component 42, thereby rigidly fixing the second electronic component 42 to second board 41. Thereby, the deterioration of the second solder 71 may be suppressed. Further, the resin applied to a portion on which stress is difficult to be concentrated may be reduced, thereby reducing the manufacturing costs of endoscope apparatus 1.

Next, a second embodiment of the present invention will be described with reference to FIG. 13. Further, in multiple embodiments described below, components having the same functions as the endoscope apparatus 1 according to the first embodiment are denoted by the same reference numerals. In addition, a portion or all of the description of the same components may be omitted.

Figure 13:
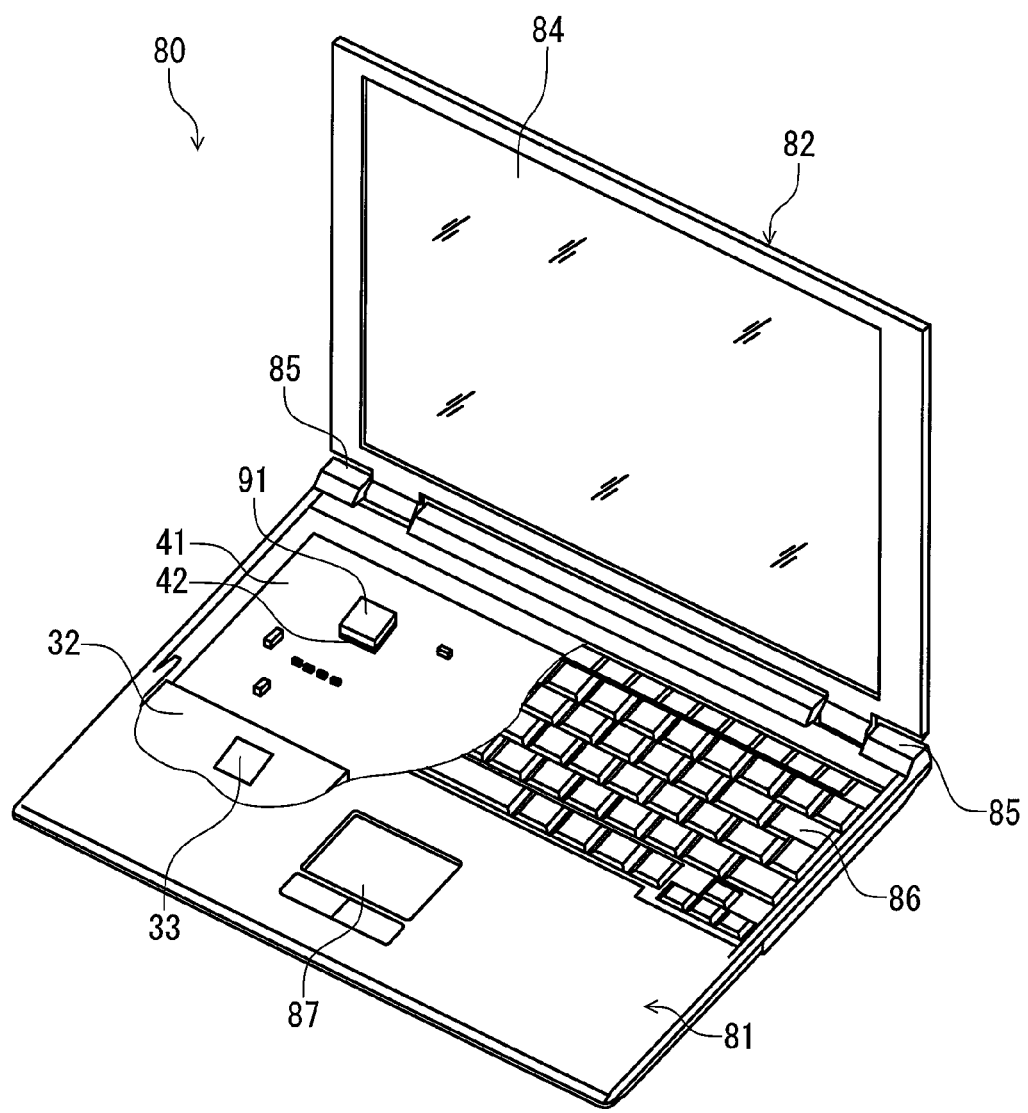
FIG. 13 is a perspective view showing a portable computer according to a second embodiment.

FIG. 13 is a perspective view showing a portable computer 80 a portion of which is being cut, according to a second embodiment. As shown in FIG. 13, the portable computer 80 includes a base 81 and a monitor 82.

The monitor 82 accommodates a display module 84 that displays images. The monitor 82 is rotatably attached to a hinge part 85 that is mounted at a rear end of the base 81. The monitor 82 rotates between a closed position horizontally disposed on the base 81 and an opened position erected from the base 81.

The base 81 includes a keyboard module 86 and a touch pad module 87. Keyboard module 86 and touch pad module 87 are installed on a top face of the base 81.

The first board 32 and the second board 41 are accommodated in the base 81. The first board 32 is, for example, a daughter board. The second board 41 is, for example, a mother board. The first electronic component 33 is mounted on the first board 32. The second electronic component 42 is mounted on the second board 41.

The first electronic component 33 is, for example, a graphic chip. The first electronic component 33 is electrically connected to the first board 32 by first solder 36, similarly to the first embodiment.

The second electronic component 42 is, for example, a CPU. The second electronic component 42 has a higher caloric value than that of the first electronic component 33. A heat sink 91 is attached to the second electronic component 42. The second electronic component 42 is electrically connected to the second board 41 by second solder 71, similarly to the first embodiment. The second electronic component 42 is fixed to the second board 41 by the bonding member 44. The second electronic component 42 is disposed so as to be spaced apart from first electronic component 33.

Since the caloric value of the second electronic component 42 is high, the periphery of the second electronic component 42 is exposed to higher heat stress than that of the periphery of the first electronic component 33. However, the second solder 71 has the higher stress resistance than that of the first solder 36 used in the main unit 3. For this reason, the deterioration of second solder 71 is suppressed.

As described above, the portable computer 80 may be the second embodiment. The embodiment is not limited thereto. Other electronic apparatus such as a desktop computer, a slate type computer, and a smart phone may also be an embodiment.

Figure 14:
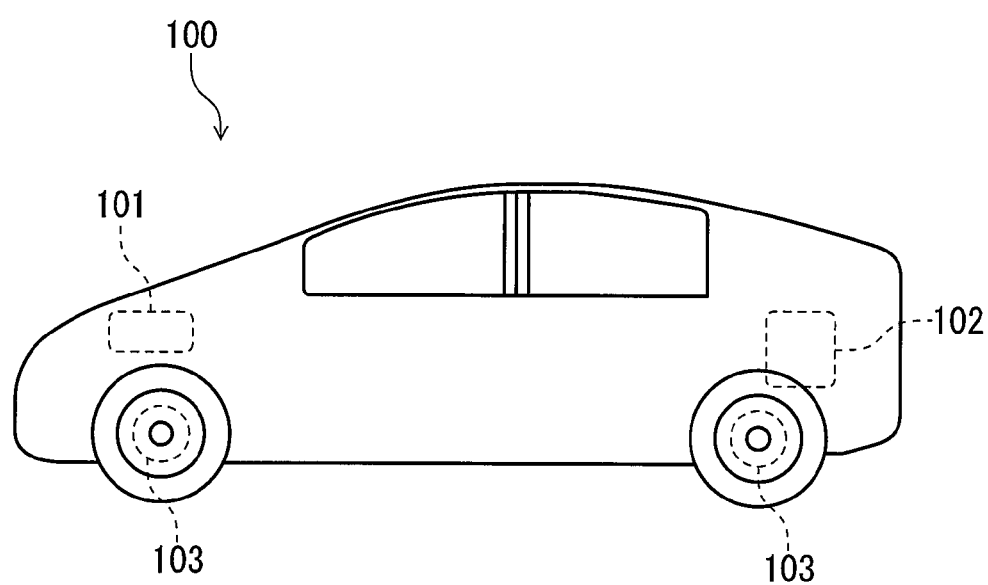
FIG. 14 is a side view schematically showing a vehicle according to a third embodiment.

Next, a third embodiment will be described with reference to FIG. 14. FIG. 14 is a side view schematically showing a vehicle 100 according to a third embodiment of the present invention. A vehicle 100 is, for example, a car and is an example of electronic apparatus.

As shown in FIG. 14, the vehicle 100 includes a computerized module 101, a battery 102, and a plurality of brake units 103.

The computerized module 101 controls the vehicle 100. The computerized module 101 includes the printed circuit board and the CPU. The printed circuit board is an example of the first board. The CPU is an example of the first electronic component. The CPU is electrically connected to the printed circuit board by the first solder 36, similarly to first electronic component 33 according to the first embodiment of the present invention. The computerized module 101 is disposed at a place where the change in temperature is relatively small.

The battery 102 is disposed at, for example, a rear portion of the vehicle 100. The battery 102 includes the printed circuit board and the chip. The printed circuit board is an example of the second board. The chip is an example of the second electronic component. The chip is electrically connected to the printed circuit board by second solder 71, similarly to the first embodiment. The chip is fixed to the printed circuit board by the bonding member 44.

For example, since the battery 102 is heat-generated at the time of supplying power, the periphery of the battery 102 is exposed to higher heat stress than that of computerized module 101. However, the second solder 71 has the higher stress resistance than that of first solder 36. For this reason, the deterioration of the second solder 71 is suppressed.

Each of the brake units 103 is disposed inside a wheel. The brake unit 103 includes the printed circuit board and an actuator. The printed circuit board is an example of the second board. The actuator is an example of the second electronic component and drives a brake pad to contact a brake disk. The actuator is electrically connected to the printed circuit board by the second solder 71, similarly to the first embodiment. The actuator is fixed to the printed circuit board by the bonding member 44.

For example, frictional heat is generated when the brake pad contacts the brake disk, such that the periphery of the brake unit 103 is exposed to the higher heat stress than that of the computerized module 101. However, the second solder 71 has the higher stress resistance than that of the first solder 36. For this reason, the deterioration of the second solder 71 is suppressed.

In the embodiment, the computerized module 101 is disposed at a place where the change in temperature is relatively small, but may be exposed to the higher heat stress by the heat generation of the CPU. For this reason, the CPU of the computerized module 101 may be electrically connected to the printed circuit board by the second solder 71. In this case, the electronic components that are mounted on, for example, the inner panel in which the change in temperature is small are electrically connected to the board by the first solder 36.

As described above, the vehicle 100 may be the third embodiment. The embodiment is not limited thereto. Other vehicles such as an electric car, a two-wheeled vehicle, or a trolley car may be an embodiment.

According to the electronic apparatus according to the embodiments as described above, the second part exposed to the higher heat stress than that of the first part is provided with the second board which is electrically connected to the second part through the second solder having a higher melting point than that of the first solder. Thereby, the deterioration caused by the heating of the solder connecting the board and the components may be suppressed.

While certain exemplary embodiment has been described, the exemplary embodiment has been presented by way of example only, and is not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An endoscope, comprising:
a first part;
a second part connected to the first part and intended to be exposed to higher heat stress than the first part;
a first board in the first part and configured to be electrically connected to a first component via a first solder;
a second board in the second part, the second board is configured to be electrically connected a second component via a second solder having a higher melting point than the first solder, and the second board is intended to be exposed to higher heat stress than the first part; and
a bonding member configured to bond the second component and the second board, the bonding member comprises a plurality of first application portions and a second application portion,
wherein the second component comprises a bottom face, a top face disposed at an opposite side of the bottom face, a lateral face which bonds the bottom face and the top face,
wherein the plurality of first application portions of the bonding member is disposed on the lateral face of a corner portion and in the vicinity of the corner portion of the second component except on the lateral face adjacent to a side portion of the top face of the second component so as to be in a state of which the side portion is exposed,
wherein the second application portion of the bonding member is disposed on the lateral face of the second component so that the second application portion is disposed between the plurality of first application on the lateral face and the second application portion is disposed from a side of the bottom face to halfway between the bottom face and the top face on the lateral face so as to be in a state of which the side portion is exposed,
wherein the bonding member has a glass transition point higher than that of the second board.

2. The apparatus of claim 1 further comprising: a first bonding member bonded to a second electronic component and a second circuit board, the first bonding member having a higher glass transition point than the second circuit board.

3. The apparatus of claim 2, wherein the second electronic component has a rectangular shape, and wherein a cross sectional shape of the first bonding member for a longer side of the second electronic component is different from a cross sectional shape of the first bonding member for a shorter side of the second electronic component.

* * * * *